United States Patent [19]

Pigerol et al.

[11] 4,209,439

[45] Jun. 24, 1980

[54] STABILIZATION OF VINYL RESINS

[75] Inventors: Charles Pigerol, Saint-Ouen; Marie-Madeleine Chandavoine; Paul de Cointet de Fillain, both of Sisteron, all of France

[73] Assignee: Labaz, Paris, France

[21] Appl. No.: 950,718

[22] Filed: Oct. 12, 1978

[30] Foreign Application Priority Data

Oct. 14, 1977 [FR] France ............................... 77 30991
Jun. 29, 1978 [FR] France ............................... 78 19518
Aug. 11, 1978 [FR] France ............................... 78 23757

[51] Int. Cl.² ............................................. C08K 5/34
[52] U.S. Cl. ........................ 260/45.8 N; 260/23 XA; 260/45.85 A; 260/45.95 H; 426/106; 426/129; 426/415
[58] Field of Search ........................... 260/45.8 N; 546/321 (U.S. only)

[56] References Cited

U.S. PATENT DOCUMENTS

| | | | |
|---|---|---|---|
| 3,637,553 | 1/1972 | Keberle et al. | 260/45.8 N |
| 3,663,558 | 5/1972 | Murayama et al. | 260/45.8 N |
| 3,883,477 | 5/1975 | Stephen | 260/45.8 N |
| 3,948,924 | 4/1976 | Giller et al. | 546/321 |
| 3,991,012 | 11/1976 | Ramey et al. | 260/45.8 N |
| 4,000,113 | 12/1976 | Stephen | 260/45.8 N |
| 4,048,171 | 9/1977 | Bossert et al. | 546/321 |
| 4,057,530 | 11/1977 | Pigerol et al. | 260/45.8 N |
| 4,096,112 | 6/1978 | Pigerol et al. | 260/45.8 N |

FOREIGN PATENT DOCUMENTS 2239496 2/1975 France .

*Primary Examiner*—Howard E. Schain
*Assistant Examiner*—R. A. White
*Attorney, Agent, or Firm*—Mason, Kolehmainen, Rathburn & Wyss

[57] ABSTRACT

Synthetic resin compositions based on vinyl polymers or copolymers are stabilized against degradation by both heat and light by the incorporation therein of a 1,4-dihydropyridine derivative represented by the general formula:

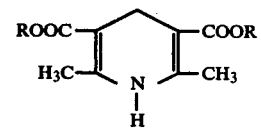

wherein R represents a straight or branched-chain saturated or unsaturated alkyl radical containing from 9 to 22 carbon atoms. The stabilizer can be present in an amount of from 0.01 to 0.5 percent by weight, based on the vinyl resin. The vinyl resin may be, for example, polyvinyl chloride, a vinyl chloride-vinyl acetate copolymer or a vinyl chloride-vinylidene chloride copolymer. The stabilized vinyl resins can be used in the manufacture of food packaging materials and containers and also of flooring tiles and recording discs.

Some of the dihydropyridine derivatives are novel compounds.

8 Claims, No Drawings

STABILIZATION OF VINYL RESINS

The present invention is concerned generally with the stabilisation of vinyl resins, including the vinyl copolymers, by means of dihydropyridine derivatives, certain of which are novel.

The stabilisers according to the invention conform to the general formula:

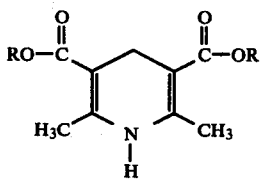
I in which R represents: a straight-chain or branched-chain, saturated or unsaturated alkyl radical, comprising from 9 to 22 carbon atoms.

Quite generally, the dihydropyridines which are used according to the invention may be prepared by the method proposed by HANTZSCH, Eisner et al, Chemical Reviews, 72, 1, 1972, which consists in causing the reaction of an acetoacetate of general formula:

II in which R assumes the same values as in formula I, with formaldehyde and ammonia, possibly formed in situ.

As regards the acetoacetates of formula II, these may be prepared in two ways:
either by action of the diketene of formula

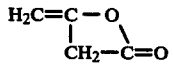

on an alcohol of formula ROH, in the presence of sodium acetate,
or by transesterification between the methyl acetoacetate and an alcohol of formula ROH,
it being understood that, in the formula ROH, R represents the same values as in formula I.

It is known that the vinyl resins have a tendency to be degraded under heat and that it is essential to introduce stabilising agents into these compositions consisting of synthetic material, with a view to retarding the degradation due to heat and hence the coloration of these compositions.

Among the organic compounds which are known for their effect in stabilising vinyl resins against heat, it is possible to mention the compounds of formula I, in which R represents an ethyl or butyl radical. The later mentioned French Pat. No. 2,239,496 does in fact show that the two above compounds thermally and chemically stabilize the vinyl resins into which they are introduced at the rate of 0.2 to 1.5% by weight.

Particularly known as a heat stabiliser is 2-phenyl indole, which is found to be of particular interest, on account of its stabilising power and its low toxicity. Moreover, it is widely used on an industrial scale for stabilising the vinyl polymers and copolymers, especially those which are used in the composition of food packaging materials.

It has surprisingly been found that the compounds according to the invention, when incorporated into a vinyl resin at the rate of 0.01 to 0.5% by weight, stabilise the said resin against light, while conferring a satisfactory thermal stability to said resin, despite the low concentration which is used.

This discovery is very important, especially in respect of the resins which are used in food packaging materials.

It is actually obvious that it would not be possible to market foods in a package of which the colouring varies over a period of time.

In addition to their photostabilising effect, it has also been discovered that the dihydropyridines according to the invention:

present a heat-stabilising action on the polyvinyl chloride at concentrations which are between 0.01 and 0.2 p.c.r. (part per 100 parts of resin).

This discovery is important, because it thereby becomes possible to visualise the use of polyvinyl chloride as thus stabilised as a packaging for food commodities. At these concentrations, the extraction of the stabiliser by the foods is extremely small if not negligible, whereas at concentrations higher than 0.2 p.c.r, it becomes considerable and does not permit of this application being considered for certain derivatives of formula I.

It has, moreover, been discovered that the extraction or migration of the stabiliser—just like its sublimation—varied with the number of carbon atoms in the chains R.

The concentration of stabiliser being used may be brought up to 1 p.c.r. when it is a question of stabilising vinyl polymers intended for uses such as the manufacture of floor coverings or recording discs.

exert a lubricating power on the vinyl resins,
permit, in the resins which contain calcium and calcium-zinc salts as primary stabilisers, of reducing the amount of zinc without as a result decreasing the stabilisation of the resin.

Now, it is known that a too high proportion of zinc causes the appearance of defects in the resin.

offer the possibility of using them at a concentration which is between 0.1 and 0.2 p.c.r. for the stabilisation of vinyl resins which contain a plasticiser, such as dioctyl phthalate.

This type of resin generally contains barium-cadmium and calcium-zinc salts as primary stabilisers and it has been established that the addition of a small quantity of a dihydropyridine according to the invention makes it possible to reduce the proportion of cadmium, which is a very expensive and toxic product, without reducing the thermal stability of the resin. Furthermore, the compounds according to the invention appreciably improve the basic shade of this type of resin, the said shade coming close to being colourless.

offer the possibility of the waste product of polyvinyl chloride, stabilised by the dihydropyridines of formula I, being recycled on machines operating by extrusion and blowing,
improve the basic shade and increase the stability of the colour of the resins containing a dye,
provide a greater antioxidising effect than, for example, that of 2,6-di-tert.-butyl-4-methyl phenol, which is an antioxidant widely used in connection with vinyl resins,
offer the possibility of advantageously replacing the stabilisers for vinyl resins as so far used, namely, 2-phenyl indole and its derivatives, the aminocrotonates of heavy alcohols or polyols and the tin derivatives, with the advantage of obtaining:

a good thermal stability at lower concentrations which are capable of being between 0.01 p.c.r. and 0.2 p.c.r., with the consequence of thereby decreasing the cost of stabilising the resin, a good resistance to light, an improvement in the initial colour of the resin and the development of the colour as a function of time.

As has already been previously mentioned, it has been established that the compounds according to the invention also exert thermostabilising and photostabilising properties on the vinyl choride copolymers (vinyl chloride - vinyl acetate, vinyl chloride-vinylidene chloride, ...). They make possible the stabilisation of the formulae which also correspond to rigid and pliable copolymers.

As regards the different applications which are involved (manufacture of recording discs, flooring tiles, pliable sheets for various packaging purposes, ... ), the compounds of formula (I) have to be incorporated into the vinyl resins in quantities which vary from 0.01 to 1 p.c.r. (part per 100 parts of resin) and preferably between 0.01 and 0.5 p.c.r.

The dihydropyridines of formula (I) are compatible with the different varieties of vinyl resins which are available on the market at the present time, as well as copolymers. By way of example, it is possible to use the following resins, which are obtained by suspension polymerisation and as listed below:

| Nature of copolymer | Commercial name | Supplier |
|---|---|---|
| Vinyl chloride-vinyl acetate with 15% of acetate | Lucovyl MA 6035 | RHONE-POULENC |
| Vinyl chloride-vinyl acetate with 15% of acetate | Lucovyl SA 6001 | RHONE-POULENC |
| Vinyl chloride-vinyl acetate with 12.5–13.5% of acetate | Vinnol H13/50 S | WACKER |
| Vinyl-chloride-vinyl acetate with 15% of acetate | Solvic 547 SA | SOLVAY |
| Vinyl chloride-vinylidene chloride with 70% of vinylidene chloride | Ixan SGA/1 | SOLVAY |

It is understood that these examples are not in any way of limiting character.

For the preparation of certain of the compositions of resins which have been tested, polyvinyl chlorides have also been used in certain cases, such as those marketed under the names:

. Lucovyl MB 1000 (supplier Rhone-Poulenc)
. Lacqvyl S.071/S (supplier ATO-CHIMIE)
. Solvic 223 (supplier Solvay).

From the tests which were carried out, it has been possible to show that:

by comparison with the same copolymers used under the same conditions, but without incorporation of this type of adjuvants, the dihydropyridines of formula (I) stabilise the vinyl copolymers with respect to heat and light in a manner without any question;

the dihydropyridines of formula (I) are shown to be decidedly better than the aminocrotonates of alcohols or of polyols for stabilising the vinyl copolymers with respect to heat and light. These observations have been essentially noted in respect of butane-1,4-diol bis-aminocrotonate, methyl aminocrotonate and the aminocrotonate of $C_{16}$-$C_{18}$ alcohols. These results have been obtained for formulae which yield rigid copolymers and flexible copolymers;

the dihydropyridines of formula (I) show thermostabilising and photostabilising properties which are very much better than those of the 2-phenyl indole which is frequently used in rigid and flexible formulae for stabilising the vinyl copolymers.

As for polyvinyl chloride, the use of the 1,4-dihydropyridines of formula (I), and especially those of high molecular weight, improves the bonding time for the formulae of copolymers which they stabilise. Particularly as regards the vinyl chloride-vinyl acetate copolymers, it has been shown that, with equimolecular concentration, the lubricating power of the didodecyl derivative of formula (I) ($R = n-C_{12}H_{25}-$) and of the compound of formula (I) resulting from Acropole 35 ($R = C_{12}H_{25}$ to $C_{15}H_{31}$, straight-chain or branched-chain) was decidedly better than that of the dimethyl derivative of formula (I) ($R = -CH_3$). The lubricating power of the dihydropyridines of formula (I) is at least comparable and generally is better than that of the aminocrotonates of alcohols or of polyols. From this point of view, the result is that it is possible to substitute the dihydropyridines of formula (I) for the aminocrotonates in certain applications, for which a good lubricating power is appreciated, as is the case with the manufacture of recording discs.

It has frequently been observed that, in the compositions under examination, the dihydropyridines of formula (I) were able to be used in amounts considerably smaller than the aminocrotonates or the 2-phenyl indole. This possibility produces an economic interest which cannot be inconsiderable as regards these molecules.

The invention is now to be described in detail, both at the level concerned with the preparation of the compounds according to the invention and at the level of their properties.

1—PREPARATION OF THE PRODUCTS 1.1—Preparation of the acetoacetates, synthesis intermediaries They were obtained by transesterification between an alcohol ROH and methyl acetoacetate. The synthesis is carried out under nitrogen in the presence of an excess of methyl acetoacetate used as reactant and solvent (3 to 4 moles of methyl acetoacetate per mole of alcohol).

The methanol which is freed is eliminated by continuous distillation until about 170° C. is reached, in the reaction medium, and then the methyl acetoacetate excess is distilled under reduced pressure (pressure of 2 to 3 mm Hg; temperature: 155°±5° C.). The quasi-total elimination of the methyl acetoacetate is important for preventing the presence of mixed dihydropyridines in the product.

The expected acetoacetate is directly used in the crude state for the continuation of the synthesis. The yield is from 95–100%.

A more specific example as regards preparation is hereinafter described:

EXAMPLE 1

Preparation of dodecyl acetoacetate

Introduced into a reactor equipped with a stirrer mechanism, a Vigreux column with a column head and a reflux condenser are 464 g (4 moles) of methyl acetoacetate and 186 g of dodecyl alcohol. The temperature of the reaction medium is progressively raised to 165° C. and the methanol having formed is distilled until the reaction is terminated, that is to say, for about 8 hours.

Oleocetyl alcohol (supplier: Henkel) is a mixture of natural fatty alcohols comprising from 12 to 20 carbon atoms (essentially from 16 to 18 carbon atoms).

| Alcohols used | | | | Acetoacetic esters prepared | |
|---|---|---|---|---|---|
| Nomenclature | Supplier | Hydroxyl index | Composition by GPC | Molecular weight | Yield |
| Dobanol 23 (straight-chain primary synthesis fatty alcohols) $C_nH_{2n+1}$—OH n = 12 to 13 Mean MW 194 MP 21°-22° | SHELL CHIMIE | 272.5 | $C_{12}$:34.9% $C_{13}$:46.4% | 289.8 | 100% |
| Dobanol 25 (straight-chain and primary synthesis fatty alcohols) $C_nH_{2n+1}$—OH n = 12 to 15 mean MW 207 MP 21°-23° | SHELL CHIMIE | 258 | $C_{12}$:20.1% $C_{13}$:27.4% $C_{14}$:25.8% $C_{15}$:14.4% | 301.4 | 95% |
| Acropole 35 (branched chain primary synthesis fatty alcohols $C_nH_{2n+1}$—OH n = 12 to 15 MW 208°-211 MP 21° C. | UGINE-KUHLMANN | 271 | $C_{12}$:20.9% $C_{13}$:51.9% $C_{15}$:15.3% | 291 | 100% |
| (1-decanol) stearyl alcohol $CH_3(CH_2)_{16}$—$CH_2OH$ MW 270 MP 56°-60° C. | LASERSON SABETIER | 195.5 | $C_{18}$:93.6% | 371 | 98% |
| Oleocetyl alcohol (mixture of natural fatty acids) MP 20°-30° C. | HENKEL | 218.3 | $C_{14}$:4% $C_{16}$:25.2% $C_{18}$:62% | 340.9 | 98.5% |
| (1-Dososanol) behenylic alcohol MW 326 MP 65°-68° C. | MERCK | 169.7 | | 410.6 | 100% |
| (Cis-9-octadecen-1-ol) oleyl alcohol MW 268 MP 13°-19° C. | GIVAUDAN | 209.3 | | | 95% |

The methyl acetoacetate excess is eliminated under a reduced pressure of 8 mm Hg and the crude dodecyl acetoacetate is recovered, and this will be used as such for the preparation of the corresponding dihydropyridine derivative (Example 3).

The general method as described above was observed for the preparation of the acetoacetates listed in the following table, these serving as synthesis intermediaries for the preparation of the corresponding derivatives of the dihydropyridines.

In this table and the following tables, the following are represented by the various abbreviations: MP: molecular weight, FP: melting point, GPC: gaseous phase chromatography, Yd.: yield, Pt: product, min.: minute, sec.: second.

The mixtures of industrial alcohols which are used and which are indicated by their commercial names are the following:

Dobanol 23 (supplier: Shell-Chimie) is a mixture of primary and straight-chain synthesis fatty alcohols having 12 or 13 carbon atoms;

Dobanol 25 (supplier: Shell-Chimie) is a mixture of primary and straight-chain synthesis fatty alcohols having from 12 to 15 carbon atoms;

Arcropole 35 (supplier: PUK) is a mixture of primary, straight-chain and branched-chain synthesis fatty alcohols having from 12 to 15 carbon atoms;

1.2—Preparation of the derivatives of 1,4-dihydropyridines of formula (I)

121. Starting from the formaldehyde and the ammonia introduced as such into the reaction medium.

EXAMPLE 2

Preparation of 2,6-dimethyl-3,5-dicarbomethoxy-1,4-dihydropyridine 23.2 g (0.2 mole) of methyl acetoacetate and 0.2 g of diethylamine are introduced into a reactor which is cooled by an ice bath. The solution is cooled to 0° C. and 7.5 g (0.1 mole) of formic aldehyde in 40 % aqueous solution are added dropwise, while ensuring that the temperature is kept below or equal to 10° C.

The reaction medium is then kept for 6 hours at 0° C. and then for 40 hours at ambient temperature.

The solution is poured off and the aqueous phase is extracted with ether, whereafter the organic phases are reunited and the solution is dried over anyhydrous sodium sulphate.

Filtration takes place and the ether is eliminated by evaporation, whereafter the oily residue is diluted with 1 part of methanol. While keeping the temperature at 0° C., ammonia is caused to bubble into the solution and then the ammonia-saturated solution is kept at ambient temperature for 12 hours. The solution is suction-filtered and the product which is obtained is recrystallised from methanol and then from acetone.

The 2,6-dimethyl-3,5-dicarbomethoxy-1,4-dihydropyridine is obtained with a yield of 86%.

Melting point: 232° C.

By operating in the same manner, the following products are prepared:

| Alkyl acetoacetate used | R | Yield | Recrystallisation solvent | M.P. |
|---|---|---|---|---|
| Ethyl acetoacetate | —CH$_2$—CH$_3$ | 75% | acetone | 196° C. |
| octyl acetoacetate | —(CH$_2$)$_7$CH$_3$ | 37% | acetone | 92° C. |
| isopropyl acetoacetate | —CH(CH$_3$)$_2$ | 83% | isopropanol | 124° C. |
| dodecyl acetoacetate | —(CH$_2$)$_{11}$CH$_3$ | 52% | acetone | 96° C. |
| cyclohexyl acetoacetate | —C$_6$H$_{11}$ | 16,5% | hexane/benzene 80/20 | 103° C. |
| propyl acetoacetate | —(CH$_2$)$_2$CH$_3$ | 36% | benzene | 148° C. |
| tert. butyl acetoacetate | —C(CH$_3$)$_3$ | 55% | benzene | 166° C. |

122. Starting from the formaldehyde and the ammonia formed in situ in the reaction medium General operating procedure Into a 1-liter reactor equipped with a reflux condenser are introduced:
crude acetoacetate: 1 mole
methanol: 320 cc
purified water: 27 g
ammonium acetate: 14.4 g
hexamethylene tetramine: 35 g.

The batch is refluxed while stirring and under a nitrogen stream. As this takes place, the mass becomes progressively limpid.

It is kept under reflux for 2½ to 3 hours and there is observed the formation of a precipitate or, according to the tests, the demixing of an oil.

After return to ambient temperature, the said temperature is maintained at —5° C./—10° C. for 2 hours, followed by suction-filtering.

The ammonium ions and the hexamethylene tetramine are then eliminated by thorough rinsing with pure water and washing is carried out with heptane in order to eliminate the corresponding puridine formed by oxidation, so as finally to dry to constant weight in a vacuum oven (50° C./10 mm Hg).

More specific embodiments of this general process are set out below:

EXAMPLE 3

Preparation of 2,6-dimethyl-3,5-dicarbododecyloxy-1,4-dihydropyridine

Into a reactor are introduced 54.0 g of dodecyl acetoacetate, 10.5 g of hexamethylene tetramine, 2.9 g of ammonium acetate, 6.5 g of methanol and 8.0 g of water.

While stirring, the temperature of the reaction medium is raised in 45 minutes to the reflux temperature of the methanol and the refluxing is maintained for 1 hour. The suspension is allowed to cool to ambient temperature and then it is poured into a mixture of 300 g of water and ice (50/50). Stirring takes place for 1 hour in order to eliminate the excess hexamethylene tetramine. Suction-filtering takes place and the product is taken up in 300 g of water. Stirring is carried out, followed by another suction-filtering operation and finally the product is recrystallised from 400 g of acetone.

The 2,6-dimethyl-3,5-dicarbododecyloxy-1,4-dihydropyridine is obtained with a yield of 73.5%.

Melting point: 96° C.

By operating in the same manner, the following products are prepared:

| Acetoacetate used | R | Yield | Recrystallisation solvent | MP |
|---|---|---|---|---|
| Phenyl acetoacetate | —C$_6$H$_5$ | 4% | dimethylformamide | 239° C. |
| p-tolyl acetoacetate | —C$_6$H$_4$—CH$_3$ | 32% | ethanol/acetone 90/10 | 214° C. |
| p-anisyl acetoacetate | —C$_6$H$_4$—OCH$_3$ | 34% | acetone | 184° C. then 195° C. |
| p-chlorophenyl acetoacetate | —C$_6$H$_4$—Cl | 14% | acetone | 227° C. |
| butyl acetoacetate | —(CH$_2$)$_3$CH$_3$ | 58% | methanol | 122° C. |
| Decyl acetoacetate | —(CH$_2$)$_9$CH$_3$ | 64% | acetone | 95° C. |
| Tetradecyl acetoacetate | —(CH$_2$)$_{13}$CH$_3$ | 65% | acetone | 96° C. |
| Octadecyl acetoacetate | —(CH$_2$)$_{17}$CH$_3$ | 78% | | 103° C. |
| Octadecenyl acetoacetate | —CH$_2$—(CH$_2$)$_7$—CH=CH—(CH$_2$)$_7$—CH$_3$ | 91,9% | | 56° C. |
| Docosanyl acetoacetate | —(CH$_2$)$_{21}$CH$_3$ | 75,6% | | 106° C. |

The last of these compounds is obtained in the form of a yellow pasty product, whereas the two preceding compounds assume the form of a yellow powder.

EXAMPLE 4

1,4-Dihydropyridines, deriving from mixtures of natural or synthetic industrial alcohols, have also been prepared and these compounds are listed below.

| Alkyl acetoacetate used | 1,4-Dihydropyridines (I) | | | | |
|---|---|---|---|---|---|
| | R | Mean MW | Yield | Appearance | MP |
| crude tri- decyl aceto- acetate (Alcohol: Acropole 35) | $CH_3(CH_2)_n$— n:11 to 14 | 574 | 76% | yellowish- green powder | 89° C. |
| crude tri- decyl aceto- acetate (Alcohol: Dobanol 23) | $CH_3(CH_2)_n$— n:11 or 12 | 572 | 45.4% | yellow powder | 89° C. |
| crude tri- decyl aceto- acetate (Alcohol: Dobanol 25) | $CH_3(CH_2)_n$— n:11 to 14 | 595 | 78% | yellowish- green powder | 89° C. |
| crude oleo- cetyl aceto- acetate (Alcohol: H.D. Ocenol) | $CH_3$—$(CH_2)_{15}$— $CH_3(CH_2)_7CH=CH(CH_2)_n$ n:6–8 | 675 | 41% | yellow powder | 81° C. |

2. Properties of the products

For simplification purposes, reference will be made to the main compounds of formula (I) as investigated and they will be represented by their code number shown in the following table.

TABLE I

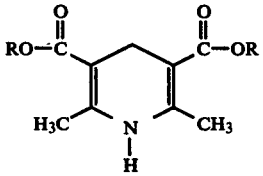

| R | CODE No. |
|---|---|
| —$CH_2$—$CH_3$ | L.28501 |
| —$(CH_2)_7$—$CH_3$ | L.28502 |
| —$CH_3$ | L.28504 |
| —CH(CH_3)_2 (isopropyl) | L.28506 |
| —$(CH_2)_{11}$—$CH_3$ | L.28507 |
| —cyclohexyl | L.28508 |
| —$(CH_2)_2CH_3$ | L.28509 |
| —$C(CH_3)_3$ | L.28510 |
| —phenyl | L.28531 |
| —$C_6H_4$—$CH_3$ | L.28538 |
| —$C_6H_4$—$OCH_3$ | L.28541 |
| —$C_6H_4$—Cl | L.28551 |

TABLE I-continued

| R | CODE No. |
|---|---|
| —$(CH_2)_3CH_3$ | L.28552 |
| —$(CH_2)_{13}CH_3$ | L.28590 |
| —$(CH_2)_9$—$CH_3$ | L.28591 |
| —$C_{12}H_{25}$ to —$C_{15}H_{31}$ (*) | L.28596 |
| —$(CH_2)_n$—$CH_3$ with n = 11 or 12 (**) | L.28597 |
| n = 11 to 14 (***) | L.28598 |
| —$(CH_2)_{17}$—$CH_3$ | L.28599 |
| —$CH_2$—$(CH_2)_7$—$CH=CH$—$(CH_2)_7$—$CH_3$ (****) | L.28600 |
| —$(CH_2)_{15}$—$CH_3$ | |
| —$(CH_2)_{21}$—$CH_3$ | L.28601 |
| —$(CH_2)_8$—$CH=CH$—$(CH_2)_7$—$CH_3$ | L.28602 |

(*) Acropole 35 $C_{12}$–$C_{15}$
(**) Dobanol 23 $C_{12}$–$C_{13}$
(***) Dobanol 25 $C_{12}$–$C_{15}$
(****) H.D. Ocenol $C_{16}$–$C_{18}$ The toxicity of the photostabilisers according to the invention was primarily established and the satisfactory results which were obtained permitted the investigation to be continued.

2.1—Study of acute toxicity

The acute toxicity of the compounds according to the invention was studied, by determining the dose of product which causes 50% death of the treated animals ($LD_{50}$).

The determination or typing is achieved by oral administration of a gummy suspension of the compounds to batches of at least 10 mice or 10 rats.

The results as observed show that, as regards these two animal species, the $LD_{50}$ is, for the molecules, higher than 2 g/kg and frequently higher than 5 g/kg.

Furthermore, no toxic symptom was found, after an observation period of 15 days.

2.2—Study of the migration

The migration or the extractability of the stabiliser from the PVC compound under the effect of various liquids (and particularly water) stored in a plastic container is of essential importance for the use of these stabilisers in the field of food packagings. The migration of the dihydropyridines (I) in water has been thoroughly investigated by comparison with the 2-phenyl indole, which is kept as reference molecule.

The technique as regards extraction was the following: using the formula which is given below, a batch of bottles (volume 1 liter, diameter 70 mm, height≃230 mm) was prepared, the said bottles being filled with a liquid simulating the foods. Under these conditions, the volume/surface ratio (volume of the liquid and surface of the bottle in contact) is close to 1.85. The migration of the stabiliser was judged by dosage of the pyridine present in the extractum, using the dosage method which is later described. This pyridine obviously represents the oxidised form of the extracted 1,4-dihydropyridine.

The investigation was particularly developed for water at 50° C. over a period of 2 months, because it represents the important problem regarding the packaging of mineral waters.

221. Formula for the manufacture of bottles

| Ingredients | Parts by weight |
| --- | --- |
| Polyvinyl chloride resin | 100 |
| Anti-shock agent | 8 |
| Epoxidised soya oil | 4 |
| Acrylic resin | 0.5 |
| Trinonyl phenyl phosphite | 0.3 |
| S L 2016 | 0.25 |
| Calcium behenate | 0.4 |
| Glyceryl trimontanate | 0.4 |
| Hydrogenated castor oil | 1.2 |
| Stabiliser | 0.015 to 0.5 |

The S L 2016 is a solution of zinc 2-ethyl hexanoate in a mixture of aromatic hydrocarbons boiling from 158° to 184° C.

222. Dosage method

The stabilisers are measured out in the form of their oxidation product (pyridine).

The oxidation is made quantitative by adding a few drops of iodine to the solution. The latter is then extracted with chloroform and the chloroform is evaporated to a small residual volume. The solution obtained is then subjected to thin-film chromatography, by comparison with solutions of known concentration of the desired pyridines.

The sensitivity threshold of this technique is 5 µg/liter.

223. Results of the investigation concerning extraction

The investigation was carried out on the following compounds:
2,6-Dimethyl-3,5-dicarbomethoxy-1,4-dihydropyridine (L. 28504).
2,6-Dimethyl-3,5-dicarboethoxy-1,4-dihydropyridine (L. 28501).
2,6-Dimethyl-3,5-dicarbobutoxy-1,4-dihydropyridine (L. 28552).
2,6-Dimethyl-3,5-dicarbododecyloxy-1,4-dihydropyridine (L. 28507).
2,6-Dimethyl-3,5-dicarbotetradecyloxy-1,4-dihydropyridine (L. 28590).
2,6-Dimethyl-3,5-dicarbooctadecyloxy-1,4-dihydropyridine (L. 28599).

| Extraction medium | STABILISER | | Migration in µg/l at 50° C. | | | |
| --- | --- | --- | --- | --- | --- | --- |
| | Nature | Concentration in pct | 10 days | 20 days | 1 month | 2 months |
| WATER | L.28504 | 0.15 | 15 | 40 | 70 | 80 |
| | L.28504 | 0.30 | 70 | 100 | 120 | 120 |
| | Control* | 0.30 | 75 | 90 | 100 | 100 |
| | L.28501 | 0.15 | 20 | 50 | 100 | 100 |
| | L.28501 | 0.30 | 90 | 120 | 150 | 150 |
| | Control | 0.30 | 70 | 90 | 100 | 100 |
| | L.28552 | 0.15 | 15 | 40 | 90 | 100 |
| | L.28552 | 0.30 | 80 | 120 | 130 | 130 |
| | Control | 0.30 | 80 | 100 | 110 | 110 |
| | L.28507 | 0.15 | <5 | <5 | <5 | <5 |
| | L.28507 | 0.30 | <5 | <5 | <5 | <5 |
| | Control | 0.30 | 75 | 90 | 100 | 100 |
| | L.28590 | 0.15 | <5 | <5 | <5 | <5 |
| | L.28590 | 0.30 | <5 | <5 | <5 | <5 |
| | Control | 0.30 | 75 | 90 | 110 | 110 |
| | L.28599 | 0.15 | <5 | <5 | <5 | <5 |
| | L.28599 | 0.30 | <5 | <5 | <5 | <5 |
| | Control | 0.30 | 70 | 90 | 120 | 130 |

*Control = 2-phenylindole

It is apparent from this investigation that
the dihydropyridines are clearly less extractable than the 2-phenyl indole,
the stabilisation of the vinyl resins by the dihydropyridines according to the invention need concentrations which are far smaller than those required by the 2-phenyl indole, the result being an even greater reduction in the migration,
in the series of 1,4-dihydropyridines (I) for which R comprises from 9 to 22 carbon atoms, the migration in the water develops according to the number of carbon atoms forming the radical R of the formula (I), this being concurrently with the sublimation, as will later be seen,
for values of R comprising from 1 to 8 carbon atoms, the migration is considerable and of the order of that generally observed for the 2-phenyl indole, i.e. from 80 to 120 µg per liter.
for values of R comprising from 1 to 8 carbon atoms, a maximum of migration seems to be observed for R=2, 3, 4 carbon atoms,
for values of R comprising from 1 to 8 carbon atoms, the migration increases with the concentration of the stabiliser in the PVC compound,
for values of R comprising from 9 to 22 carbon atoms, and particularly for R=12, 14 and 18 carbon atoms, the migration in the water is below 5 µg/l, whatever the concentration of the stabiliser in the PVC compound between 0.01 and 0.5 p.c.r., (p.c.r.=part percent, parts of resin). In fact, the migration has to be clearly smaller than 5 µg/liter, but this estimation is limited to this value by the sensitivity threshold of the technique used for the dosage.

It can be concluded therefrom that the dihydropyridines (I), of which the radical R varies between 9 and 22 carbon atoms, are capable of being used for stabilising the PVC intended for the packaging of mineral waters, whereas those in which R varies between 1 and 8 carbon atoms are not suitable for this purpose, because of their too high migration.

For justifying the possibility of using the dihydropyridines (I) having a radical R comprising from 9 to 22 carbon atoms in applications concerned with food packaging, other than those applications relating to mineral waters, the extractability of the dihydropyridines by several solutions or solvents having the following composition, by weight, was investigated:
(a) water-sodium chloride: 97-3
(b) water-saccharose: 90-10
(c) water-sodium chloride-acetic acid: 98.5-0.5-1
(d) water-citric acid (solution at pH=5): 98-2
(e) water-acetic acid: 97-3
(f) water-acetic acid: 90-10
(g) water-ethanol: 85-15
(h) water-acetic acid: 50-50
(i) water-ethanol: 50-50
(j) pure heptane: 50-50

The results obtained are set out in the following tables:

| EXTRACTION MEDIUM | STABILISER 0.3 per | Migration in μg/l at 50° C. | |
|---|---|---|---|
| | | 1 month | 2 months |
| | Phenyl-2 indole | 90 | 140 |
| | L.28504 | 100 | 120 |
| H₂O/NaCl | L.28501 | 120 | 150 |
| (97:3) | L.28552 | 80 | 100 |
| | L.28507 | <5 | <5 |
| | L.28590 | <5 | <5 |
| | L.28599 | <5 | <5 |
| Water/Sacchrose | L.28504 | 100 | 100 |
| (90:10) | L.28507 | <5 | <5 |
| Water/NaCl/CH₃COOH | L.28504 | 110 | 120 |
| (98,5:0,5:1) | L.28507 | <5 | <5 |
| Water/citric | L.28504 | 110 | 130 |
| acid* (98:2) | L.28507 | <5 | <5 |
| Water/CH₃COOH | L.28504 | 90 | 120 |
| (97:3) | L.28507 | <5 | <5 |
| Water/CH₃COOH | L.28504 | 120 | 140 |
| (90:10) | L.28507 | <5 | <5 |
| Water/C₂H₅OH | L.28504 | 150 | 180 |
| (85:15) | L.28507 | <5 | <5 |
| Water/CH₃COOH | L.28504 | 150 | 200 |
| (50:50) | L.28507 | 25 | — |
| Water/C₂H₅OH | L.28504 | 250 | — |
| (50:50) | L.28507 | 50 | — |

*The pH of this solution is adjusted to 5 with aqueous caustic soda solution.

| | STABILISER 0.3 per | Migration in μg/l at 50° C. | |
|---|---|---|---|
| | | after 36 h. | after 84 h. |
| Heptane | L.28504 | 300 | 390 |
| | L.28507 | 120 | 150 |

It is apparent from these results that the dihydropyridines (I) in which R comprises from 9 to 22 carbon atoms, and especially those in which R comprises 12, 14 and 18 carbon atoms, give a migration smaller than 5 μg/l of solution in respect of the solutions a, b, c, d, e, f and g. Under the same conditions, the first terms of the dihydropyridine series (I) and particularly that of which the radical R=—CH₃, give migrations of the order of 80 to 100 μg/l, which are comparable with those of 2-phenyl indole.

For the solutions h, i and j, the dihydropyridines (I) in which R comprises from 9 to 22 carbon atoms, likewise give better results than their lower homologues and 2-phenyl indole.

23—Study of the sublimation

The sublimation of the stabiliser is to be taken into account within the sphere of protecting the health of the personnel of the factories where the stabiliser is manufactured or used. In other words, it is a question involving the safety at work.

In this respect, it has been confirmed that:
the sublimation of the 1,4-dihydropyridines is not only related to the molecular weight. It has in fact been observed that, contrary to that which might be expected, the derivative (I) for which R=—CH₃ is sublimed appreciably less than the dihydropyridines (I) having a heavier radical R, such as ethyl, propyl, isopropyl, butyl, etc.

Thus, under the operating conditions reserved for judging the sublimation of the products of this series, the 2-phenyl indole chosen as reference molecule is sublimed at the rate of 62% of the quantity of product being used. Under the same conditions, the derivative (I), for which R=—CH₃ (methyl), is sublimed to 34% and the higher homologues, (ethyl, propyl, isopropyl, butyl, etc.) to a higher percentage which is between 35 and 98%.

The sublimation is important for the values of R representing 1 to 8 carbon atoms, whether these radicals are saturated or unsaturated, straight-chain or branched-chain radicals. Under the working conditions later described, the quantity of sublimed product is between 10 and 98%. It is lowered to 7% for R=straight-chain octyl, and this still represents a considerable sublimation.

The sublimation becomes small, i.e. equal to or lower than 3%, starting with the radical having 9 carbon atoms and more particularly starting from the radical comprising 10 carbon atoms.

The sublimation of the dihydropyridines (I) having a radical R which comprises from 10 to 22 carbon atoms is very small (in all cases less than 2%), and sometimes even zero, for the saturated straight-chain radicals comprising 12, 14, 16, 18, 22 carbon atoms and for the straight-chain and unsaturated radicals, such as the oleylic chain. These findings are valid for mixtures of these different dihydropyridines (example R=oleocetyl radical).

The sublimation of the dihydropyridines (I) having a radical R which is derived from synthesised alcohols available on the market, such as Acropole 35, Dobanol 23, Dobanol 25 (straight-chain or branched-chain synthesis alcohols comprising from 12 to 15 carbon atoms) remains small (2 to 3%) but higher than that of the straight-chain radicals. These synthesis alcohols do in fact contain a large part of branched alcohols in the α-position, since they are prepared by oxo reaction on straight-chain olefines.

It is clearly seen from this last finding that the problem of the sublimation is not connected only with the molecular weight of the dihydropyridine (I) under consideration, but also its structure. In particular, with equal or comparable molecular weights, a straight-chain radical R seems to lead to a smaller sublimation than a branched-chain radical R.

The calculated data which justify these observations are set out below.

2—Sublimation results

231. Operating procedure

A test sample of about 130 mg of the product to be investigated is introduced into a 100 cc beaker. The latter is placed in a 250 cc reactor. The temperature is kept at 160° C. by means of a thermostatically controlled oil bath for 6 hours, the atmosphere of the reactor being inert (nitrogen) in order to avoid the oxidation of the 1,4-dihydropyridine into pyridine, which is more sublimable.

232. Results

For each dihydropyridine derivative which is investigated, the result is expressed as a percentage of sublimed product relatively to the quantity being used.

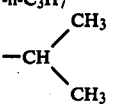

| Product | | % of sublimed product |
|---|---|---|
| 2-phenylindole | | 62% |
| | $CH_3$ | 34.2% |
| | $-C_2H_5$ | 82.9% |
| | $-n-C_3H_7$ | 79.1% |
| | $-CH\begin{smallmatrix}CH_3\\CH_3\end{smallmatrix}$ | 98.1% |
| Dihydropyridines of formula (I) with R signifying | $-(CH_2)_3-CH_3$ | 39.2% |
| | $-(CH_2)_7-CH_3$ | 7.2% |
| | $-(CH_2)_9-CH_3$ | 1.7% |
| | $-(CH_2)_{11}-CH_3$ | 1.7% |
| | $-(CH_2)_{13}-CH_3$ | 0.1% |
| | $-(CH_2)_{17}-CH_3$ | 1.2% |
| | $-(CH_2)_{21}-CH_3$ | 0.4% |
| | $CH_3-(CH_2)_n-$ * <br> n = 11 a 12 | 3.1% |
| | $CH_3-(CH_2)_n-$ ** <br> n = 11 to 14 | 3.1% |
| | $C_{12}H_{25}$ to $C_{15}H_{31}$ *** | 3.2% |
| | $\{CH_3(CH_2)_7-CH=CH-(CH_2)_n-$ **** <br> $CH_3(CH_2)_{15}-$  n = 6-8 | 1.7% |

*prepared from Dobanol 23
**prepared from Dobanol 25
***prepared from Acropole 35
****prepared from H.D. Ocenol 2.4—Investigation of the photostabilising power A comparative study of the photostabilising power of the compounds of the invention was carried out by sheets of polyvinyl chloride, which only differ from one another by the stabiliser which is used, being exposed to the sun.

The two reference stabilisers were:
2-(3'-methoxy-4'-hydroxyphenyl)-indole (S. 3630)
2-phenyl indole (S. 3621).

EXAMPLE 5

Two compositions of polyvinyl chloride were prepared in accordance with the following formula:

| Ingredients | Parts by weight |
|---|---|
| Polyvinyl chloride resin | 100 |
| Anti-shock resin | 8 |
| Epoxidised soya oil | 4 |
| Acrylic resin | 0.5 |
| Trinonyl phenyl phosphite | 0.3 |
| SL 2016 | 0.25 |
| Calcium behenate | 0.4 |
| Hydrogenated castor oil | 0.2 |
| Glyceryl trimontanate | 0.4 |
| Stabiliser | 0.2 |

The stabilised polyvinyl chloride sheets were prepared by mixing on a cylinder at 160° C. and were exposed to the sun under the same conditions.

Their colouring was evaluated in two different ways, after 6 hours and 12 hours exposure to the sun:
on the sheets themselves, by comparison with the Gardner scale, described in French Pat. No. 2,273,841,
on a solution of these sheets in tetrahydrofuran by comparison with the scale described in Pharmacopée Francaise (9th Edition, II, 338).

The results obtained are set out in the following table:

| Stabilisers | Colour of the sheets according to GARDNER | | | Colour of the sheets according to the Pharmacopee | | |
|---|---|---|---|---|---|---|
| | Exposure time | | | Exposure time | | |
| | 0 | 6h | 12h | 0 | 6h | 12h |
| S 3630 | 1 | 4 | 8 | B5 | B4 to JB4 | B3 to JB3 |
| S 3621 | 2 | 3 | 6 | J6 | J5 | J4 |
| L 28504 | 1 | 1 | 1.5 | JV6 | JV6 | JV6 |
| L 28501 | 1 | 1 | 1.5 | JV6 | JV6 | JV6 |

Four other molecules were tested (R=n—$C_{10}H_{22}$ (L. 28591; n—$C_{12}H_{25}$ (L. 28507); —$C_{14}H_{29}$ (L.28590); —$C_{18}H_{37}$ (L.28599)) by comparison with the molecules studied above (R=—$CH_3$; R=—$C_2H_5$) with the assistance of the same formula and with 0.2 p.c.r. of stabiliser.

The development of the coloration of the stabilised PVC was judged in the same manner.

The results as observed show a comparable photostabilising power between these different dihydropyridines, whatever the molecular weight.

Similar tests were carried out on various formulae of copolymers.

EXAMPLE 6

Comparison of the dihydropyridines according to the invention (abbreviation DHP) with 2-phenyl indole flexible vinyl copolymer formula vinyl cloride-vinyl acetate copolymer.

| Formula: | Lucovyl SA 6001 | 100 parts |
|---|---|---|
| | dioctyl phthalate | 40 parts |
| | calcium stearate | 2 parts |
| | melamine | 2 parts |
| | wax E | 1 part |
| | stabiliser | 0.3 part. |

-continued

| Test | Stabiliser | Time in hours | Coloration in degrees Gardner | |
|---|---|---|---|---|
| | | at time 0 | after 24 hours | |
| A | 2-Phenyl indole | 1 | 6 | |
| | L.28504 | 1 | 1 | |
| | L.28591 | 1 | 1 | |
| | L.28541 | 1 | 4 | |
| | L.28599 | 1 | 1 | |
| | L.28601 | 1 | 1 | |
| | L.28602 | 1 | 1 | |
| B | 2-Phenyl indole | 1 | 8 | |
| | L.28507 | 1 | 1 | |
| | L.28502 | 1 | 1 | |
| | L.28506 | 1 | 2 | |
| | L.28508 | 1 | 2 | |

EXAMPLE 7

Comparison of the DHP with 2-phenyl indole rigid vinyl copolymer formula vinyl chloride-vinylidene chloride copolymer.

| Formula: | Resin Solvic 223 | 90 parts |
|---|---|---|
| | copolymer IXAN SGA 1 | 10 parts |
| | reinforcing agent BTA III | 8 parts |
| | epoxidised soya oil | 4 parts |
| | calcium stearate | 0.2 parts |
| | zinc stearate | 0.1 part |
| | Lubricant 4146 | 1.2 part |
| | Lubricant 6164 | 0.4 part |
| | Stabiliser | 0.3 part |

The lubricant 4146 is a hydrogenated castor oil and the lubricant 6164 is glyceryl trimontanate.

| Stabiliser | Time in hours | Coloration in degrees Gardner | |
|---|---|---|---|
| | | at time 0 | after 120 hours |
| 2-Phenyl indole | | 1.5 | 17 |
| L. 28504 | | 1.5 | 4 |
| L. 28507 | | 1.5 | 4 |

EXAMPLE 8

Comparison of the DHP with 2-phenyl indole rigid vinyl copolymer formula vinyl cloride-vinylidene chloride copolymer.

| Formula: | PVC resin Solvic 223 | 90 parts |
|---|---|---|
| | copolymer IXAN SGA/1 | 10 parts |
| | reinforcing agent BTA III | 8 parts |
| | epoxidised soya oil | 4 parts |
| | calcium stearate | 0.2 part |
| | zinc stearate | 0.1 part |
| | Lubricant 4146 | 1.2 part |
| | Lubricant 6164 | 0.4 part |
| | stabilizer | 0.3 part |

| Stabiliser | Time in hours | Coloration in degrees Gardner | |
|---|---|---|---|
| | | at time 0 | after 24 hours |
| 2-Phenyl indole | | 1 | 13 |
| L. 28597 | | 1 | 2 |
| L. 28601 | | 1 | 2 |
| L. 28541 | | 1 | 3 |

EXAMPLE 9

Comparison of the DHP with 2-phenyl indole rigid vinyl copolymer formula vinyl chloride-vinylidene chloride copolymer.

Formula: identical with that of Example 8, but with a variable concentration x of stabiliser.

| Stabiliser | Time in hours | Concentration x | Coloration in degrees Gardner | |
|---|---|---|---|---|
| | | | at time 0 | after 24 hours |
| 2-Phenyl indole | | 0.3 part | 1 | 13 |
| L. 28504 | | 0.3 part | 1 | 2 |
| L. 28507 | | 0.3 part | 1 | 2 |
| L. 28504 | | 0.15 part | 1 | 2 |
| L. 28507 | | 0.7 part | 1 | 2 |

The results of Example 9 prove, with the variations in concentrations of the products L.28504 and L.28507, that the copolymers in which they are incorporated are stable to light. In effect, variations in concentration from 0.15 to 0.7 p.c.r. do not seem to have any influence on the resistance of the copolymers to light.

2.5—Study of the thermostabilising power

251. Static thermostability

The static thermostability was investigated by the method described in French Pat. No. 2,273,841, 2-phenyl indole being the reference substance.

The stabiliser is incorporated, with other usual additives, into a polyvinyl chloride resin in powder form. A rigid sheet is formed by the mixture being calendered at 160° C. and this sheet is placed for periods of variable duration in a fixed temperature oven (185° C. or 210° C.) until carbonisation commences.

The colour of the samples is then compared with the Gardner colour scale.

Investigation was carried out with the following resins:

EXAMPLE 10

| Ingredients | Parts by weight |
|---|---|
| Polyvinyl chloride | 100 |
| anti-shock resin | 9 |
| epoxidised soya oil | 2 |
| calcium 2-hydroxy stearate | 0.2 |
| S L 2016 | 0.1 |
| stabiliser | 0.3 or $1.55 \times 10^{-3}$ mole |

The following results were obtained after a resin containing 0.3 part of stabiliser had been in an oven at 210° C.

| Stabiliser | Time in minutes | | | | | | |
|---|---|---|---|---|---|---|---|
| | 0 | 3 | 6 | 9 | 12 | 15 | 18 |
| L.28501 | 1 | 1 | 2 | 2 | 4 | 8.5 | B |
| L.28506 | 1 | 1 | 2 | 5 | 11 | 19 | B |
| L.28507 | 1 | 1 | 2 | 6 | 8 | 19 | B |
| L.28508 | 1 | 1 | 3 | 5 | 14 | B | |
| L.28509 | 1 | 1 | 2 | 4 | 4 | 17 | B |
| L.28510 | 1 | 1 | 4 | 5 | 15 | B | |
| L.28504 | 1 | 1 | 2 | 3 | 7.5 | 19 | B |
| 2-phenylindole | 1 | 2 | 2 | 10 | 11 | 16 | B |
| L.28504 | 1 | 1 | 1 | 3 | 7 | B | |
| 2-phenylindole | 1 | 1 | 2 | 4 | 13 | 17 | B |
| L.28538 | 1 | 1 | 3 | 3 | 4 | 14 | B |
| L.28541 | 1 | 1 | 1.5 | 3 | 5 | 11 | B |
| L.28504 | 1 | 1 | 1 | 2.5 | 3 | 11 | B |
| 2-phenylindole | 1 | 2 | 2 | 3 | 6 | 14 | B |

-continued

| Stabiliser | Time in minutes | | | | | | |
|---|---|---|---|---|---|---|---|
| | 0 | 3 | 6 | 9 | 12 | 15 | 18 |
| L.28552 | 1 | 1 | 2 | 4 | 11 | 12 | B |
| L.28504 | 1 | 1 | 2 | 3 | 8 | 10 | B |
| 2-phenylindole | 1 | 1 | 2 | 6 | 14 | 14 | B |

The above results show the clear superiority of the dihydropyridines according to the invention as compared with 2-phenyl indole.

Tests were also carried out at 185° C., with a resin containing 0.3 part of stabiliser, and the results obtained are set out in the table below:

| Stabi- liser | Time in minutes | | | | | | | | | |
|---|---|---|---|---|---|---|---|---|---|---|
| | 0 | 6 | 12 | 18 | 24 | 27 | 30 | 33 | 36 | 39 | 42 |
| L.28501 | 1 | 1 | 2 | 8 | 11 | 13 | 13 | 18 | B | | |
| L.28531 | 1 | 1 | 3 | 7 | 10 | 10 | 10 | 16 | B | | |
| L.28538 | 1 | 1 | 3 | 10 | 13 | 13 | 14 | 17 | 17 | B | |
| L.28504 | 1 | 1 | 2 | 7 | 11 | 11 | 11 | 13 | B | | |
| 2-phenyl- indole | 1 | 1 | 3 | 5 | 13 | 13 | 14 | 14 | 15 | 15 | B |
| L.28506 | 1 | 1 | 3 | 3 | 6 | 12 | 13 | 14 | 15 | 15 | 17 |
| L.28508 | 1 | 1 | 3 | 5 | 8 | 13 | 16 | 18 | 18 | 18 | |
| L.28509 | 1 | 1 | 2 | 3 | 5 | 9 | 9 | 11 | 13 | 14 | 15 |
| L.28510 | 1 | 1 | 2 | 4 | 10 | 18 | 18 | 19 | 19 | B | |
| L.28504 | 1 | 1 | 1 | 2 | 4 | 7 | 7 | 8 | 10 | 11 | 15 |
| 2-phenyl- indole | 1 | 1 | 3 | 5 | 10.5 | 13 | 14 | 14 | 14 | 14 | 14 |
| L.28507 | 1 | 2 | 2 | 7 | 11 | 13 | 14 | 15 | 15 | 18 | B |
| L.28504 | 1 | 1 | 2 | 3 | 5 | 7.5 | 8.5 | 9 | 14 | B | |
| 2-phenyl- indole | 1 | 1 | 4 | 9 | 13 | 14 | 14 | 14 | 14 | 15 | 15 |
| L.28502 | 1 | 1 | 2 | 3 | 4 | 6 | 7 | 8.5 | 9 | 11 | 15 |
| L.28504 | 1 | 1 | 2 | 3 | 4 | 7 | 7 | 8 | 9 | 11 | 14 |
| 2-phenyl- indole | 1 | 1 | 3 | 9.5 | 11 | 14 | 14 | 14 | 14 | 14 | 14 |

The above results also show the obvious superiority of the dihydropyridines according to the invention over 2-phenyl indole.

Tests were also carried out at 185° C. with resins containing equimolecular quantities of stabiliser, namely $1.55 \times 1^{-3}$ mole, and the following results were obtained:

| Stabi- liser | Wt. of stabi- liser | Time in minutes | | | | | | | | | |
|---|---|---|---|---|---|---|---|---|---|---|---|
| | | 0 | 6 | 12 | 18 | 24 | 27 | 30 | 33 | 36 | 39 | 42 |
| L.28501 | 0.4 | 1 | 1 | 1 | 5 | 10 | 11 | B | | | | |
| L.28531 | 0.5 | 1 | 1 | 2 | 5 | 8.5 | 10.5 | 11 | 16 | B | | |
| L.28538 | 0.6 | 1 | 1 | 2 | 7 | 7 | 9 | 10 | 17 | B | | |
| L.28541 | 0.6 | 1 | 1 | 2 | 7 | 9 | 9 | 10 | 16 | B | | |
| L.28504 | 0.35 | 1 | 1 | 1 | 4 | 5 | 8 | 11 | 15 | B | | |
| 2-phenyl- indole | 0.3 | 1 | 2 | 3 | 10 | 13 | 13 | 13 | 14 | 16 | 16 | B |

The superiority of the dihydropyridines over 2-pheyl indole is also confirmed when they are used in the same molecular quantity as this latter.

Similar tests were carried out on derivatives of dihydropyridines of which the chain R comprises more carbon atoms.

The following formula was used:

| PVC resin (Solvic 223) | 100 parts |
|---|---|
| anti-shock resin | 9 parts |
| epoxidised soya oil | 2 parts |
| SL 2016 | 0.1 part |
| SS 32 | 0.2 part |
| Stabiliser | x (x = 0.1 to 0.3 p.c.r.) |

The product SS 32 is calcium hydroxystearate.

Use was made of the experimental methods described above for obtaining the stability bands and their examination, by employing the evidence of stability at 210° C. in an oven.

With equal quantities, the various dihydropyridines (I) give comparable results, whatever the value of the radical R. The fact of increasing the molecular weight of (I) does not lower its thermostabilising power and concentrations which vary from 0.01 to 0.5 p.c.r. and especially from 0.01 to 0.2 p.c.r. lead to very good results.

The results as obtained are set out below.

| Stabiliser L | Time in minutes | | | | | |
|---|---|---|---|---|---|---|
| | 0 | 3 | 6 | 9 | 12 | 15 |
| 28.597 | 1 | 1 | 1 | 2 | 4 | 7 |
| 28.598 | 1 | 1 | 1 | 2 | 4 | 13 |
| 28.596 | 1 | 1 | 1 | 2 | 4 | 13 |
| 28.599 | 1 | 1 | 1 | 2 | 4 | 13 |
| 28.600 | 1 | 1 | 1 | 2 | 5 | 13 |
| 2-phenylindole | 1 | 1 | 2 | 4 | 11 | 14 |

| Stabiliser L | Time in minutes | | | | |
|---|---|---|---|---|---|
| | 0 | 3 | 6 | 9 | 12 |
| 28.601 | 1 | 1 | 2 | 2 | 4 |
| 28.507 | 1 | 1 | 2 | 2 | 3 |
| 2-phenylindole | 1 | 1 | 2 | 4 | 10 |

| Quantity of stabiliser in the formula: 0.2 p.c.r. | | | | | | | |
|---|---|---|---|---|---|---|---|
| Stabiliser L | Time in minutes | | | | | | |
| | 0 | 2 | 4 | 6 | 8 | 10 | 12 | 14 |
| 28.597 | 1 | 1 | 1 | 2 | 3 | 3 | 11 | 11 |
| 28.598 | 1 | 1 | 1 | 2 | 3 | 3 | 11 | 15 |
| 28.596 | 1 | 1 | 1 | 2 | 3 | 3 | 11 | 13 |
| 28.599 | 1 | <2 | <2 | 2 | 3 | 3 | 10.5 | 14 |
| 28.600 | 1 | <2 | <2 | 2 | <3 | <3 | 10.5 | 14 |
| 2-phenylindole | 1 | 1 | 1 | 2 | 3 | 4 | 12 | 15 |

| Stabiliser L | Time in minutes | | | | | |
|---|---|---|---|---|---|---|
| | 0 | 2 | 4 | 6 | 8 | 10 | 12 |
| 28.502 | 1 | 1 | 1 | 2 | 2 | 3 | 5 |
| 28.590 | 1 | 1 | 1 | 2 | 2 | 3 | 7 |
| 28.591 | 1 | 1 | 1 | 2 | 2 | 3 | 8 |
| 28.507 | 1 | 1 | 1 | 2 | 2 | 3 | 7.5 |
| 2-phenylindole | 1 | 1 | 1 | 2 | 2 | 5 | 9 |

| Quantity of stabiliser in the formula: 0.1 p.c.r. | | | | | | | |
|---|---|---|---|---|---|---|---|
| Stabiliser L | Time in minutes | | | | | | |
| | 0 | 2 | 4 | 6 | 8 | 10 | 12 |
| 28.502 | 2 | 2 | 2 | 2 | 3 | 6 | 11 |
| 28.590 | 2 | 2 | 2 | 2 | 2 | 4 | 10.5 |
| 28.591 | 2 | 2 | 2 | 2 | 2 | 4 | 10.5 |
| 28.507 | 2 | 2 | 2 | 2 | 3 | 4 | 10.5 |
| 2-phenylindole | 2 | 2 | 2 | 3 | 4 | 11 | 13 |

5.2—Stabilisation of the resins intended for the bottling of mineral waters

The tests were carried out in the following manner: a resin which contains calcium stearate, zinc stearate and epoxidised soya oil in addition to the stabiliser which is to be tested was mixed on a cylinder-type mixer and the stability of the initial colour was noted, that is to say, the time elapsing between the commencement of the mixing and the first visible change in the colour of the resin was measured. The thermal stability of the resin was also observed, i.e. the time elapsing between the commencement of the mixing and the degradation of the resin was measured, a like resin was passed through an extrusion and blowing machine and the development of the colour of the resin was observed at each of the three passages through the machine.

For this extrusion-blowing operation, the following characteristics were retained:
Temperature: 165°–160°–165°–160°–180° C. Screw speed: 60 r.p.m.
Die: gap:1.5 mm, land: 55 mm
Mould: cylindrical bottle of 250 cc.

Four resins, numbered from 1 to 4 and respectively containing 0.2 part of 2-phenyl indole, 0.2, 0.03 and 0.015 part of the compound L. 28504, were tested and the following results were obtained:

|  | Resin | | | |
|---|---|---|---|---|
| Mixing at 220° C. | 1 | 2 | 3 | 4 |
| Colour stability in minutes | 3 | 6 | 3 | 2 |
| Thermal stability in minutes | 13 | 13.5 | 12.7 | 12.3 |
| Bottle colour at | | | | |
| 1st passage | Sky blue | Bright sky blue | Bright sky blue | Bright sky blue |
| 2nd passage | Blue, toning towards green | Bright sky blue | Bright sky blue | Bright sky blue |
| 3rd passage | Greenish blue | Bright sky blue | Bright sky blue | Bright sky blue |

It can be confirmed that 2,6-dimethyl-3,5-dicarbomethoxy-1,4-dihydropyridine imparts to the resin a colour stability which is more marked than that of 2-phenyl indole, even at a rate of 0.015 part per cent of parts of resin.

The same tests are carried out, but with a resin containing different proportions of zinc and calcium stearate.

| Stabiliser | Quantity of stabiliser | | | | | | | | |
|---|---|---|---|---|---|---|---|---|---|
| No of resin | 1 | 2 | 3 | 4 | 5 | 6 | 7 | 8 | 9 |
| Calcium stearate | 0.29 | 0.29 | 0.29 | 0.29 | 0.29 | 0.29 | 0.29 | 0.29 | 0.15 |
| Zinc stearate | 0.32 | 0.32 | 0.32 | 0.32 | 0.32 | 0.15 | — | 0.32 | — |
| 2-Phenyl indole | 0.15 | — | — | — | — | — | — | — | — |
| L.28504 | — | 0.15 | 0.075 | 0.05 | 0.03 | 0.015 | 0.15 | 0.15 | 0.075 |

The following results were obtained:

|  | Resin | | | | | | | | |
|---|---|---|---|---|---|---|---|---|---|
| Mixing at 220° C. | 1 | 2 | 3 | 4 | 5 | 6 | 7 | 8 | 9 |
| Colour stability in minutes | 2 to 3 | 5 | 4 | 4 | 3 | 3 | 3 | <1 | 3 |
| Heat stability in minutes | 9 | 9 | 8.5 | 8.5 | 8.5 | 8.5 | 15.5 | <7 | 5 |

As in the preceding test, the compound L.28504 improves the colour and the stability. Compound L.28504 has proved to be 10 to 15 times more efficient than 2-phenyl indole.

In formula No. 2, the compound L.28504 does not have any direct influence on the heat stability, but it permits, while preserving the colour shade, of reducing the amount of zinc stearate, which may cause the appearance of defects in the resin.

As regards the examination of the colouring of the resin after each passage through the extruder and blowing machine, the excellent behaviour of the resins containing compound L.28504 has been confirmed.

253. Stabilisation of the plasticised resins

Sheets of polyvinyl chloride, previously mixed for 5 minutes at 180° C., were pressed for 5 minutes at 170° C., and the colour stability and the heat stability after mixing, and then the coloration of the sheets after pressing, were observed.

As adjuvants, as well as the stabiliser to be tested, the resin in question contains wax E, dioctyl phthalate, barium stearate and cadmium stearate, in the following proportions:

| Ingredients | Quantities | | | | | | | | |
|---|---|---|---|---|---|---|---|---|---|
| No. of resin | 1 | 2 | 3 | 4 | 5 | 6 | 7 | 8 | 9 |
| Polyvinyl chloride resin | 100 | 100 | 100 | 100 | 100 | 100 | 100 | 100 | 100 |
| E wax | 0.3 | 0.3 | 0.3 | 0.3 | 0.3 | 0.3 | 0.3 | 0.3 | 0.3 |
| Dioctyl phthalate | 50 | 50 | 50 | 50 | 50 | 50 | 50 | 50 | 50 |
| Barium stearate | — | 0.375 | — | 0.375 | 0.375 | 0.375 | 0.375 | 0.375 | 0.375 |
| Cadmium stearate | — | — | 0.375 | 0.375 | 0.375 | 0.15 | 0.15 | 0.05 | 0.05 |
| Compound | — | — | — | — | 0.1 | — | 0.05 | — | 0.05 |

The following results were obtained:

| Mixing at 180° C. | 1 | 2 | 3 | 4 | 5 | 6 | 7 | 8 | 9 |
|---|---|---|---|---|---|---|---|---|---|
| Colour stability in minutes | 25 | 25 | 25 | 35 | 50 | 30 | 45 | 20 | 35 |
| Thermal stability in minutes | 25 | 5 | 25 | 35 | 50 | 30 | 55 | 25 | 50 |
| Pressing at 170° C. Colour shade of | — | — | — | Pink- | Very | Pink- | Very | Red- | Yellow- |

| | | | | | |
|---|---|---|---|---|---|
| the pressed sheet (thickness: 3 mm) | | ish | slightly yellowish | slightly yellowish | dish ish |

The above results show that the compound L.28504 substantially improves the basic shade and clearly increases the thermal stability.

It is also established that the presence of the compound L.28504 permits a reduction in the proportion of cadmium sterate, which is a very costly and toxic product.

Finally, the thermal or heat stabilisation of the vinyl copolymers by the dihydropyridines was investigated.

EXAMPLE 11

Rigid copolymer formula vinyl chloride-vinyl acetate copolymer.

| Formula: | Lucovyl MA 6035 | 80 parts |
|---|---|---|
| | Lucovyl MB 1000 | 20 parts |
| | calcium stearate | 0.5 part |
| | stabiliser | 0.3 part |

Examination of the stability in a ventilated oven at 185° C.

| | Time in minutes | | | | | | | |
|---|---|---|---|---|---|---|---|---|
| Stabiliser | 0 | 2 | 4 | 6 | 8 | 10 | 12 | 14 |
| No stabiliser | 1 | 2 | 4 | 7 | 13 | 16 | 17 | 18 |
| L.28599 | 1 | 1 | 3 | 6 | 10 | 14 | 16 | 17 |
| L.28601 | 1 | 1 | 4 | 9 | 11 | 14 | 16 | 17 |
| L.28602 | 1 | 1 | 4 | 9 | 12 | 16 | 17 | 18 |
| L.28502 | 1 | 1 | 3 | 6 | 10 | 13 | 14 | 18 |

Comment: The colorations expressed in degrees Gardner are favourable as regards the formulae stabilised by the dihydropyridines according to the invention. However, in actual fact, the figures only inadequately show the spacings, because the copolymer which is not stabilised shows a relatively intense colour formation from the zero time, which it is difficlt to indicate in the Gardner scale.

EXAMPLE 12

Rigid copolymer formula vinyl clorlde-vinyl acetate copolymer.

| Formula: | Lucovyl MA 6035 | 80 parts |
|---|---|---|
| | Lucovyl MB 1000 | 20 parts |
| | calcium stearate | 0.5 part |
| | stabiliser | 0.1 part |

Examination of the stability in a ventilated oven at 185° C.

| | Time in minutes | | | | | | | |
|---|---|---|---|---|---|---|---|---|
| Stabiliser L | 0 | 2 | 4 | 6 | 8 | 10 | 12 | 14 |
| No stabiliser | 1.5 | 2 | 4 | 11.5 | 15 | 17 | 18 | 18.5 |
| L.28504 | 1 | 1 | 4 | 6 | 11 | 11 | 12 | 13 |
| L.28507 | 1 | 1 | 4 | 10 | 12 | 13 | 15 | — |
| L.28597 | 1 | 1 | 4 | 10 | 12 | 15 | 17— | |

The comment made in connection with Example 11 is also applicable.

EXAMPLE 13:

Flexible copolymer formula vinyl chloride-vinyl acetate copolymer.

| Formula: | Lucovyl MA 6035 | 100 parts |
|---|---|---|
| | dioctyl phthalate | 60 parts |
| | melamine | 2 parts |
| | calcium stearate | 2 parts |
| | stabiliser | 0.2 part |

Gelling: 5 minutes at 120° C.

Passage through a Metrastat oven at 160° C.: time 60 minutes rate of flow 50 1/hour.

| | Time in minutes | | | | |
|---|---|---|---|---|---|
| Stabiliser L | 0 | 30 | 40 | 50 | 60 |
| Without stabiliser | 1 | 6 | 13 | 14 | 17 |
| L.28504 | 1 | 1 | 2 | 4 | 12 |
| L.28507 | 1 | 2 | 6 | 12 | 15 |

EXAMPLE 14: Flexible copolymer formula vinyl chloride-vinyl acetate copolymer.

| Formula: | Lucovyl SA 6001 | 100 |
|---|---|---|
| | dioctyl phthalate | 40 parts |
| | calcium stearate | 2 parts |
| | melamine | 2 parts |
| | stabiliser | 0.3 part |

Passage through a Metrastat oven at 160° C.: time 60 minutes rate of flow 50 1/hour

| | Time in minutes | | | | | |
|---|---|---|---|---|---|---|
| stabiliser L | 0 | 10 | 20 | 30 | 40 | 50 | 60 |
| Without stabiliser | 1 | 1 | 5 | 8 | 12 | 13 | 13 |
| L.28504 | 1 | 1 | 2 | 6 | 8 | 10 | 12 |
| L.28507 | 1 | 1 | 2 | 6 | 8 | 10 | 12 |

EXAMPLE 15

Rigid copolymer formula vinyl chloride-vinylidene chloride copolymer.

| Formula: | Solvic 223 | 90 parts |
|---|---|---|
| | IXAN SGA/1 | 10 parts |
| | Reinforcing agent BTA III | 8 parts |
| | Epoxidised soya oil | 4 parts |
| | calcium stearate | 0.2 part |
| | zinc stearate | 0.1 part |
| | Lubricant 4146 | 1.2 part |
| | Lubricant 6164 | 0.4 part |
| | stabiliser | 0.3 part |

Passage through a ventilated oven at 210° C.

| | Time in minutes | | | | |
|---|---|---|---|---|---|
| Stabiliser L | 0 | 3 | 6 | 9 | 12 | 15 |
| Without stabiliser | 2 | 2 | 5 | 10.5 | 14 | 16 |
| L.28504 | 1.5 | 1.5 | 2 | 3 | 10 | 13 |
| L.28507 | 1.5 | 1.5 | 3 | 4 | 12.5 | 15 |

The comment made with respect to Example No. 1 is also applicable.

EXAMPLE 16

Rigid copolymer formula vinyl chloride-vinylidene chloride copolymer.

| Formula: | Solvic 223 | 90 parts |
|---|---|---|
| | IXAN SGA/1 | 10 parts |
| | Reinforcing agent BTA III | 8 parts |
| | Epoxidised soya oil | 4 parts |

-continued

| | |
|---|---|
| Calcium stearate | 0.2 part |
| Zinc stearate | 0.1 part |
| Lubricant 4146 | 1.2 part |
| Lubricant 6164 | 0.4 part |
| Stabiliser | 0.3 part |

Passage through ventilated oven at 210° C.

| Stabiliser L | Time in minutes | | | | |
|---|---|---|---|---|---|
| | 0 | 3 | 6 | 9 | 2 |
| Without stabiliser | 1.5 | 2.5 | 4.5 | 11 | 14 |
| L.28597 | 1 | 1 | 2 | 4 | 12.5 |
| L.28601 | 1 | 1 | 2 | 5 | 13.5 |

The comment made with respect to Example 11 is also applicable.

The dihydropyridines of formula I (DHP) were compared with the β-aminocrotonates of alcohols and of polyols.

The following Examples 17 to 29 show the superiority of the thermostabilising power of the 1,4-dihydropyridines of formula (I) over that of the β-aminocrotonates.

EXAMPLE 17

Comparison of the DHP with the butane-1,4-diol-β-aminocrotonate and the methyl β-aminocrotonate. Rigid copolymer formula vinyl chloride-vinyl acetate copolymer

| Formula: | Lucovyl MA 6035 | 80 parts |
|---|---|---|
| | Lucovyl MB 1000 | 20 parts |
| | Calcium stearate | 0.5 part |
| | Stabiliser | 0.5 part |

Passage through ventilated oven at 185° C.

| Stabiliser | Time in minutes | | | | | | |
|---|---|---|---|---|---|---|---|
| | 0 | 2 | 4 | 6 | 8 | 10 | 12 |
| Butane-1,4-diol-β-aminocrotonate | 1 | 1 | 4 | 10 | 13 | 15 | 18 |
| Methyl β-amino crotonate | 1 | 1 | 5 | 12 | 14 | 17 | 18 |
| L.28504 | 1 | 1 | 1 | 5 | 8 | 11.5 | 13.5 |

EXAMPLE 18

Comparison of the DHP compounds with the stabiliser $G_1$ (stabiliser $G_1$ is a mixture at present in use and consisting of butane-1,4-diol-bis-β-aminocrotonate and of $C_{16}$–$C_{18}$ alcohol β-aminocrotonates) rigid vinyl copolymer formula vinyl chloride-vinyl acetate copolymer.

| Formula: | Resin, Solvic 547 S.A | 80 parts |
|---|---|---|
| | Resin, Lacqvyl S-071-S | 20 parts |
| | Calcium stearate | 0.5 part |
| | Irgawax 280 | 0.1 part |
| | Stabiliser | 0.3 part |

Passage in a ventilated oven at 185° C.

| Stabiliser | Quantity of stabiliser | Time in minutes | | | | | | | |
|---|---|---|---|---|---|---|---|---|---|
| | | 0 | 2 | 4 | 6 | 8 | 10 | 12 | 14 |
| Stabiliser $G_1$ | 0.3 part | 1.5 | 1.5 | 2 | 3.5 | 4 | 12.5 | 15 | 18 |
| L.28504 | 0.3 part | 1 | 1 | 1 | 2 | 3 | 4 | 7 | 13 |
| L.28507 | 0.3 part | 1 | 1 | 1 | 2.5 | 4 | 7 | 10.5 | 17 |

EXAMPLE 19

Comparison of the DHP compounds with the stabiliser $G_1$ rigid vinyl copolymer formula vinyl chloride-vinyl acetate copolymer.

| Formula: | Lucovyl MA 6035 | 80 parts |
|---|---|---|
| | Lucovyl MB 1000 | 20 parts |
| | Calcium stearate | 0.5 part |
| | Stabiliser $G_1$ or DHP | 0.5 part |

Passage in ventilated oven at 185° C.

| Stabiliser | Time in minutes | | | | | | |
|---|---|---|---|---|---|---|---|
| | 0 | 2 | 4 | 6 | 8 | 10 | 12 |
| Stabiliser $G_1$ | 1 | 1 | 4 | 11 | 12.5 | 16 | 18.5 |
| L.28501 | 1 | 1 | 2 | 7 | 12 | 15 | — |
| L.28504 | 1 | 1 | 1.5 | 6 | 9.5 | 13 | 17 |

EXAMPLE 20

Comparison of the DHP compounds with the stabiliser $G_1$. Rigid vinyl copolymer formula vinyl chloride-vinyl acetate copolymer.

| Formula: | Lucovyl MA 6035 | 80 parts |
|---|---|---|
| | Lucovyl MB 1000 | 20 parts |
| | Calcium stearate | 0.5 part |
| | Stabiliser $G_1$ or DHP | 0.5 part |

Passage in ventilated oven at 185° C.

| Stabiliser | Time in minutes | | | | | | |
|---|---|---|---|---|---|---|---|
| | 0 | 2 | 4 | 6 | 8 | 10 | 12 |
| Stabiliser $G_1$ | 1 | 1 | 2.5 | 11 | 13.5 | 17 | 18.5 |
| L.28597 | 1 | 1 | 2 | 3 | 11 | 13 | — |
| L.28599 | 1 | 1 | 2.5 | 3 | 11 | 15 | — |
| L.28601 | 1 | 1 | 3 | 6 | 13 | 17 | — |

EXAMPLE 21

Comparison of the DHP compounds with the stabiliser $G_1$. Rigid vinyl copolymer formula vinyl chloride-vinyl acetate copolymer.

| Formula: | Vinnol H 13/50 S | 100 parts |
|---|---|---|
| | Glyceryl tribehenate | 0.4 part |
| | Calcium stearate | 0.5 part |
| | $G_1$ or DHP stabiliser | 0.5 part |

Stability in a ventilated oven at 185° C.

| Stabiliser | Time in minutes | | | | | | | |
|---|---|---|---|---|---|---|---|---|
| | 0 | 2 | 4 | 6 | 8 | 10 | 12 | 14 |
| Stabiliser $G_1$ | 1 | 2 | 3 | 4 | 9 | 12 | 18 | — |
| L.28504 | 1 | 1 | 2 | 3 | 4 | 11 | 18 | — |

EXAMPLE 22

Comparison of the DHP compounds with stabiliser $G_1$ rigid vinyl copolymer formula vinyl chloride-vinyl acetate copolymer.

| Formula: | Lucovyl MA 6035 | 80 parts |
|---|---|---|
| | Lucovyl MB 1000 | 20 parts |
| | Calcium stearate | 0.5 part |
| | DHP or $G_1$ stabiliser | 0.3 part |

Stability in ventilated oven at 185° C.

| Stabiliser | Time in minutes | | | | | | |
|---|---|---|---|---|---|---|---|
| | 0 | 2 | 4 | 6 | 8 | 10 | 12 | 14 |
| Stabiliser $G_1$ | 1 | 1 | 2 | 3 | 6 | 10 | 12.5 | 16 |
| L.28504 | 1 | 1 | 2 | 3 | 4 | 6 | 9 | 13 |

| | | | | | | | | |
|---|---|---|---|---|---|---|---|---|
| L.28507 | 1 | 1 | 2 | 4 | 5 | 9 | 10 | — |
| L.28597 | 1 | 1 | 2 | 3 | 5 | 8 | 11 | — |

EXAMPLE 23

Comparison of the DHP compounds with stabiliser $G_1$ rigid vinyl copolymer formula vinyl chloride-vinyl acetate copolymer.

| Formula: | Lucovyl MA 6035 | 80 parts |
|---|---|---|
| | Lucovyl MB 1000 | 20 parts |
| | Calcium stearate | 0.5 part |
| | DHP or $G_1$ stabiliser | 0.1 part |

Stability in ventilated oven at 185° C.

| | Time in minutes | | | | | | | |
|---|---|---|---|---|---|---|---|---|
| Stabiliser | 0 | 2 | 4 | 6 | 8 | 10 | 12 | 14 |
| Stabiliser $G_1$ | 1 | 1 | 6 | 7 | 11 | 12 | 14 | 16 |
| L.28599 | 1 | 1 | 4 | 6 | 10 | 11 | 12.5 | — |
| L.28601 | 1 | 1 | 4 | 6 | 10 | 11 | 13 | — |
| L.28501 | 1 | 1 | 2 | 4 | 10 | 11 | 14 | — |
| L.28506 | 1 | 1 | 2 | 6 | 10 | 12 | 14 | — |

EXAMPLE 24

Comparison of the DHP compounds with the stabiliser $G_1$ rigid vinyl copolymer formula vinyl chloride-vinyl acetate copolymer.

| Formula: | Lucovyl MA 6035 | 80 parts |
|---|---|---|
| | Lucovyl MB 1000 | 20 parts |
| | Calcium stearate | 0.5 part |
| | DHP or $G_1$ stabiliser | 0.3 part |

Stability in ventilated oven at 185° C.

| | Time in minutes | | | | | | |
|---|---|---|---|---|---|---|---|
| Stabiliser | 0 | 2 | 4 | 6 | 8 | 10 | 12 | 14 |
| Stabiliser $G_1$ | 1 | 1 | 2 | 6 | 11.5 | 16 | 18 | burnt |
| L.28541 | 1 | 1 | 2 | 5 | 10 | 12 | 13 | 16 |

EXAMPLE 25

Comparison of the DHP compounds with the stabiliser $G_1$ rigid vinyl copolymer formula vinyl chloride-vinyl acetate copolymer.

| Formula: | Lucovyl MA 6035 | 80 parts |
|---|---|---|
| | Lucovyl MB 1000 | 20 parts |
| | Calcium stearate | 0.5 part |
| | Stabiliser | 0.1 part |

Stability in ventilated oven at 185° C.

| | Time in minutes | | | | | | |
|---|---|---|---|---|---|---|---|
| Stabiliser | 0 | 2 | 4 | 6 | 8 | 10 | 12 |
| Stabiliser $G_1$ | 1 | 1 | 2 | 6 | 13 | 16 | 18 |
| L.28541 | 1 | 1 | 2 | 4 | 12 | 13 | 17 |

EXAMPLE 26

Comparison of the DHP compounds with 2-phenyl indole rigid vinyl copolymer formula vinyl chloride-vinyl acetate copolymer.

| Formula: | Lucovyl MA 6025 | 80 parts |
|---|---|---|
| | Lucovyl MB 1000 | 20 parts |
| | Calcium stearate | 0.5 part |
| | Stabiliser | 0.3 part |

Stability in ventilated oven at 185° C.

| | Time in minutes | | | | | | | |
|---|---|---|---|---|---|---|---|---|
| Stabiliser | 0 | 2 | 4 | 6 | 8 | 10 | 12 | 14 |
| 2-Phenyl indole | 1 | 1 | 2 | 3 | 8 | 12 | 14 | 17 |
| L.28504 | 1 | 1 | 2 | 3 | 5.5 | 8 | 12 | 15 |
| L.28507 | 1 | 1 | 2 | 3 | 10 | 11 | 16 | 17.5 |

EXAMPLE 27

Comparison of the DHP compounds with 2-phenyl indole rigid vinyl copolymer formula vinyl chloride-vinyl acetate copolymer.

| Formula: | Lucovyl MA 6035 | 80 parts |
|---|---|---|
| | Lucovyl MB 1000 | 20 parts |
| | Calcium stearate | 0.5 part |
| | Stabiliser | 0.1 part |

Stability in ventilated oven at 185° C.

| | Time in minutes | | | | | | | |
|---|---|---|---|---|---|---|---|---|
| Stabiliser | 0 | 2 | 4 | 6 | 8 | 10 | 12 | 14 |
| 2-Phenyl indole | 1 | 1 | 2 | 3.5 | 10.5 | 13 | 16 | 18 |
| L.28504 | 1 | 1 | 2 | 3 | 7 | 11 | 13 | 17 |

EXAMPLE 28

Comparison of the DHP compounds with 2-phenyl indole rigid vinyl copolymer formula vinyl chloride-vinylidene chloride copolymer.

| Formula: | PVC resin, Solvic 223 | 90 parts |
|---|---|---|
| | Copolymer IXAN SGA/1 | 10 parts |
| | Reinforcing agent BTA III | 8 parts |
| | Epoxidised soya oil | 4 parts |
| | Calcium stearate | 0.2 part |
| | Zinc stearate | 0.1 part |
| | Lubricant 4146 | 1.2 part |
| | Lubricant 6164 | 0.4 part |
| | Stabiliser | 0.3 part |

Passage in ventilated oven at 210° C.

| | Time in minutes | | | | | |
|---|---|---|---|---|---|---|
| Stabiliser | 0 | 3 | 6 | 9 | 12 | 15 |
| 2-Phenyl indole | 2 | 2 | 5 | 8.5 | 14 | 16 |
| L.28504 | 1.5 | 1.5 | 2 | 3 | 10 | — |
| L.28507 | 1.5 | 1.5 | 3 | 4 | 12.5 | 15 |

EXAMPLE 29

Comparison of the DHP compounds with 2-phenyl indole rigid vinyl copolymer formula vinyl chloride-vinylidene chloride copolymer.

| Formula: | PVC resin, Solvic 223 | 90 parts |
|---|---|---|
| | Copolymer IXAN SGA/1 | 10 parts |
| | Reinforcing agent BTA III | 8 parts |
| | Epoxidised soya oil | 4 parts |
| | Calcium stearate | 0.2 part |
| | Zinc stearate | 0.1 part |
| | Lubricant 4146 | 1.2 part |
| | Lubricant 6164 | 0.4 part |
| | Stabiliser | x part |

Passage in ventilated oven at 210° C.

| | Quantity | | | | | |
|---|---|---|---|---|---|---|
| Time in minutes | x of | | | | | |
| Stabiliser | stabiliser | 0 | 3 | 6 | 9 | 12 |
| 2-Phenyl indole | 0.3 part | 1 | 1 | 4 | 10 | 15 |
| L.28597 | " | 1 | 1 | 2 | 4 | 12.5 |
| L.28601 | " | 1 | 1 | 2 | 5 | 14 |
| L.28541 | " | 1 | 1 | 2 | 4 | 8 |

| | | | | | | |
|---|---|---|---|---|---|---|
| L.28504 | " | 1 | 1 | 1.5 | 3.5 | 5 |
| L.28507 | " | 1 | 1 | 2 | 5 | 8.5 |
| L.28507 | 0.7 part | 1 | 1 | 2 | 5 | 7 |
| L.28504 | 0.15 part | 1 | 1 | 1.5 | 3.5 | 5.5 |

The results which are set out in the foregoing table show that:

the dihydropyridines of formula (I) may be effective as thermostabilisers of the vinyl copolymers with a concentration which is smaller in the formula than the 2-phenyl indole, a concentration of 0.15 p.c.r. of dihydropyridine of formula (I), and of L.28504 in particular, leads to a better result than 0.3 p.c.r. of 2-phenyl indole, the use of certain dihydropyridines of formula (I) instead of 2-phenyl indole may provide an undoubted economic interest, the increase in the quantity of a dihydropyridine of formula (I), such as L.28507, in the formula improves the stabilisation time but has practically no influence on the colouring of the copolymer during the first 10 minutes of the heating period.

2.6 —Study of the antioxidant power

This study was carried out in two periods:

it was shown that the dihydropyridines according to the invention has antioxidant properties better than those of the known antioxidants, such as hydroquinone, 4-methoxy phenol and di-tert.-2,6-butyl-4-methyl phenol, it was shown that the antioxidant power of the dihydropyridines according to the invention, directly on a vinyl resin, is superior by comparison with an anti-oxidant very widely used in this field, namely, di-tert.-2,6-butyl-4-methyl phenol.

261. Polarographic study of the oxidation potential

EXAMPLE 30

(a) Working conditions

Electrodes reference electrode: a calomel electrode which contains, as junction liquid, a saturated solution of anhydrous lithium perchlorate working electrode: rotating electrode of vitreous carbon (2500 r.p.m.)

counter-electrode: platinum.

Chemical products acetonitrile, having a water content smaller than 0.1% and not presenting any polarographic waves between −2.5 volts and +2.5 volts.

anhydrous lithium perchlorate with a water content smaller than 1%.

Reagents 0.1 M solution of lithium perchlorate in acetonitrile, treated and preserved on a molecular screen of 4 Å.

Polarographic conditions voltage: 10 mV initial potential: OV exploration amplitude: 0 to 2 V exploration speed: 10 mV/sec.

sensitivity: 1.25 µA to 50 µA —mean concentration $0.3 \cdot 10^{-3}$ mole/liter.

Precaution: Between each measurement, the vitreous carbon electrode and the platinum electrode are carefully cleaned with Joseph paper.

The results given below were obtained:

| Products | Oxidation potential |
|---|---|
| Compound L 28504 | 0.74 ± 0.01 |
| Compound L.28501 | 0.73 ± 0.01 |
| Di-tert.-2,6-butyl-4-methyl phenol | 1.11 ± 0.02 |
| tert.-2-butyl-4-methoxy phenol | 0.81 ± 0.01 |
| Hydroquinone | 0.83 ± 0.01 |
| 4-Methoxy phenol | 0.89 ± 0.01 |

The values found show that the dihydropyridines according to the invention have a greater reducing power than the reference antioxidants.

EXAMPLE 31

(a) Working conditions

Electrodes platinum counter-electrode and calomel electrode with filling by a saturated aqueous solution of lithium chloride.

Reagent

The measurements were carried out in the following solvent:

90 parts of an 0.1 M solution of lithium perchlorate in methanol, 10 parts of a 0.1 M solution of perchloric acid in acetic acid.

Polarographic conditions square voltage superimposed with constant pulses of +10 millivolts, initial potential: 500 millivolts, scanning voltage: 1000 millivolts in the anode direction, oxidation at the vitreous carbon electrode (speed of rotation: 2000 r.p.m.)

temperature: 35° C.

The definitive results were achieved at the concentration of 0.5 m.mole/liter for the BHT, a dihydropyridine derivative of low molecular weight (L.28504: R=methyl) and three heavy dihydropyridine derivatives (L.28507: R=dodecyl, L.28602: R=oleyl, L.28590: R=myristyl).

(b) Results

The following table indicates the values as obtained in millivolts, for the oxidation potential and the nature of the radical R of the corresponding formula I.

| Tested products | Oxidation potential |
|---|---|
| BHT | + 1163 millivolts |
| L.28504 | + 850 millivolts |
| L.28507 | + 783 millivolts |
| L.28602 | + 808 millivolts |
| L.28590 | + 732 millivolts |

The following conclusions are reached from an examination of these results:

the dihydropyridines (I) have an oxidation potential which is clearly smaller than that of the BHT and, as a consequence, more powerful antioxidising properties;

the heavy dihydropyridines (I) (L.28507–L.28590–L.28602) have an oxidising potential smaller than that of the lightest dihydropyridine (I) (R=—CH₃; L.28504) and, as a consequence, show better antioxidising properties.

262. Study of the antioxidising power on a vinyl resin

The investigation was carried out with the following resin, which contains, as antioxidising agent, either the compound L.28504 or BHT.

| Ingredients | Parts by weight |
|---|---|
| Polyvinyl chloride resin | 100 |
| Anti-shock agent | 10 |
| Acrylic resin | 0.5 |
| Epoxidised soya oil | 3 |
| SL 2016 | 0.1 |
| Calcium and zinc stearates | 0.2 |
| Hydrogenated castor oil | 1.5 |
| Polyethylene wax | 0.3 |
| Antioxidant | 0.05 to 1 |

The stability bands were examined:
in a conventional oven at 185° C., every 10 minutes, for 80 minutes,
a Metrastat oven at 210° C., for 1 hour.

The coloration was calculated according to the Gardner scale.
The following results were obtained.

| Concen- | Antioxy- | (a) oven at 185° C. Time in minutes | | | | | | | | |
|---|---|---|---|---|---|---|---|---|---|---|
| trations | dant | 0 | 10 | 20 | 30 | 40 | 50 | 60 | 70 | 80 |
| 0.05 | BHT | >1 | 1+ | 2− | 5− | >6 | 7 | 7 | 8 | B |
|  | L.28504 | 1 | 1 | 1+ | 3+ | 4− | 6+ | 7 | 8 | B |
| 0.1 | BHT | >1 | 1+ | 2− | >5 | >6 | 7 | 7 | 8 | B |
|  | L.28504 | 1 | 1 | 1+ | <2 | 3+ | 5+ | 7 | 7 | B |
| 0.2 | BHT | >1 | 1+ | 2+ | 5− | >6 | 7 | 7 | 8 | B |
|  | L.28504 | 1 | 1 | 1 | 1+ | 2 | 3 | 5 | >6 | B |
| 0.3 | BHT | <1+ | 1+ | >2 | >6 | 7 | 8 | 8 | 8+ | B |
|  | L.28504 | 1 | 1 | 1 | 1 | 2 | >2 | 8 | 8 | B |
| 0.4 | BHT | <1+ | >1+ | 3 | >6 | 8− | 9 | 9 | 9 | B |
|  | L.28504 | 1 | 1 | 1 | 1 | 1+ | >2+ | 4 | 8 | B |
| 0.5 | BHT | <1+ | >1+ | 3 | >6 | >7 | 8− | 8 | 8 | B |
|  | L.28504 | 1 | 1 | 1 | >1 | 1+ | >2+ | 4− | 8 | B |
| 1 | BHT | 1+ | 2− | >3 | 8 | 8 | 8 | 9 | 9 | B |
|  | L.28504 | 1 | 1 | 1 | 1 | 1+ | 4 | 8 | B | — |

The symbol "B" indicates "burnt", while the index "+" signifies that the colour is disposed half-way between the lower unit and the upper half-unit. Similarly, the index "−" signifies that the colour is between the lower half-unit and the upper unit. Finally, it was considered, for example, that >2 means that it is between 2 and 2+.

It may be concluded from the above results that the compound L.28504 is very clearly better than the reference compound, for 50 minutes, and for all the antioxidant concentrations.

| Concen- | Antioxy- | (b) Metrastat oven at 210° C. Time on minutes | | | | | |
|---|---|---|---|---|---|---|---|
| tration | dant | 0 to 10 | 10 to 20 | 20 to 25 | 25 to 30 | 30 to 35 | 35 to 40 |
| 0,05 | BHT | 2− | 2 | 3− | 4+ | 10 | >10, B at 38 |
|  | L.28504 | 1 | 1 | 1 | 1 | 5 | >10, B at 40 |
| 0,1 | BHT | 2− | 2 | 3− | 4+ | 11 | >11, B at 39 |
|  | L.28504 | 1 | 1 | 1 | 1 | 5 | >10, B at 38 |
| 0,2 | BHT | 2− | 2 | 3− | 4+ | 11 | >11, B at 39 |
|  | L.28504 | 1 | 1 | 1 | 1 | 5− | <9, B at 39 |
| 0,3 | BHT | <1 | 2− | 3− | 3 | 9 | <10, B at 39 |
|  | L.28504 | 1 | 1 | 1 | 1 | 3+ | <6, B at 39 |
| 0,4 | BHT | 2− | 2 | 3 | 3+ | 10 | >10, B at 38 |
|  | L.28504 | 1 | 1 | 1 | 1 | 4− | 6−, B at 38 |
| 0,5 | BHT | 2− | 2 | 3 | 3+ | 10+ | >10+, B at 38 |
|  | L.28504 | 1 | 1 | 1 | 1 | 3+ | 6, B at 38 |
| 1 | BHT | 2− | 2 | 3− | 5 | 11 | >11, B at 38 |
|  | L.28504 | 1 | 1 | 1 | 1 | 2+ | >2+, B at 37 |

The results also show the clear superiority of the compound L.28504 over the reference compound.

It is necessary to point out that, from the zero time, the sheets containing the BHT show a pink colouring, and this represents another disadvantage of the BHT.

2.7—Study of the lubricating power

The lubricating power was judged by the adhesion time, which was determined on a calender-type mixer, equipped with heating cylinders, and compared with that of a reference stabiliser.

EXAMPLE 32

The temperature of the cylinders was from 165°–170° C. and the reference stabiliser was the stabiliser $G_1$.

| Formula investigated: | |
|---|---|
| Solvic 547 SA | 80 parts |
| Lacqvyl S.071/S | 20 parts |
| Irgawax 280 | 0.1 part |
| Calcium stearate | 0.5 part |
| Stabiliser | from 0.3 to 0.8 part |

Results

| No. of tests | | | Quantity of stabiliser p.c.r. | | | | |
|---|---|---|---|---|---|---|---|
| Stabiliser | 1 | 2 | 3 | 4 | 5 | 6 | 7 |
| L.28504 | 0.3 | | | | | | |
| L.28507 | | 0.3 | 0.7 | | | | |
| L.28596 | | | | 0.3 | 0.8 | | |
| Stabiliser $G_1$ | | | | | | 0.3 | 0.7 |
| Adhesion time | 12 min | 12 min 45 sec | 17 min 30 sec | 12 min 30 sec | 17 min 20 sec | 12 min | 16 min 20 sec |

These results show that:
with equal concentration (0.3 p.c.r.), the dihydropyridines of formula (I) and the stabiliser $G_1$ have a very closely related adhesion time, with an advantage for the dihydropyridines of high molecular weight (L.28507 and L.28596).
with equimolecular concentration (0.3 p.c.r. for L.28504, 0.7 p.c.r. for L.28507, 0.8 p.c.r. for L.28596), the lubricating power of L.28507 and of L.28596 is definitely better than that of L.28504,
disregarding the concentration, the lubricating power of the dihydropyridines of formula (I) is at least comparable with that of the stabiliser $G_1$. It is better as regards L.28507 and L.28596. It is shown by this comparison that the dihydropyridines may be used in place of the aminocrotonates, for example, for the manufacture of recording discs.

EXAMPLE 33

The temperature of the cylinders was from 180°–190° C. and the reference stabiliser was 2-phenyl indole.

| Formula investigated | |
|---|---|
| . PVC resin (Solvic 223) | 100 parts |
| . Anti-shock resin (BTA III) | 8 parts |
| . Epoxidised soya oil | 2 parts |
| . Stabiliser | x parts |

Working conditions on the calender-type mixer:
Front cylinder: temperature 190° C.
Rear cylinder: temperature 180° C.

| PRODUCTS | R | x (pcr) | Adhesion time | |
|---|---|---|---|---|
| L.28504 | —CH₃ | 0,5 | 12 min. | 17 sec. |
| L.28501 | —C₂H₅ | 0,5 | 11 min. | 25 sec. |
| L.28506 | —CH(CH₃)₂ | 0,5 | 8 min. | 0 sec. |
| | | 0,527 | 8 min. | 30 sec. |
| | | 0,555 | 9 min. | 0 sec. |
| L.28502 | —(CH₂)₇—CH₃ | 0,5 | 12 min. | 19 sec. |
| | | 0,665 | 13 min. | 25 sec. |
| | | 0,83 | 15 min. | 25 sec. |
| L.28591 | —(CH₂)₉—CH₃ | 0,5 | 13 min. | 29 sec. |
| | | 0,72 | 16 min. | 10 sec. |

| | | | | |
|---|---|---|---|---|
| | | 0,94 | 18 min. | 30 sec. |
| L.28507 | —(CH₂)₁₁—CH₃ | 0,5 | 14 min. | 36 sec. |
| | | 0,775 | 19 min. | 10 sec. |
| | | 1,05 | 22 min. | 45 sec. |

It becomes apparent from these results that, within the series of dihydropyridine molecules (I), those of which the radical R contains from 9 to 22 carbon atoms lead to an adhesion time which is decidedly better than that observed in respect of the lower homologues, when they are used in equimolecular quantities or equal quantities. This improvement in the adhesion time represents 15 to 50% of the mean adhesion time of the group of the dihydropyridines, of which the radical R varies between 1 and 8 carbon atoms.

In particular, the 2,6-dimethyl-3,5-dicarbododecyloxy-1,4-dihydropyridine shows a considerable improvement in the adhesion time in all the formulae which have been examined.

These properties are to be emphasised, because they are capable of reducing the expense involved in the stabilisation, by making possible a reduction in the amount of lubricants or an improvement in the passage of the PVC compound on the machines which carry out the extrusion and the blowing.

The fact of increasing the dimension of the radical R in the formula (I) thus enables this general structure to be given three interesting properties, which are not possessed by the lower homologues ($R < C_8$) of the series, and this limits the use of these lower homologues and extends to the exclusion thereof in the foodstuff field (migration). However, the increase in the molecular weight does not modify the photostabilising and thermostabilising properties of these molecules by comparison with the lower homologues.

We claim:

1. A synthetic resin composition comprising a vinyl chloride homo-polymer or copolymer and, in an amount at least sufficient to impart stabilisation against degradation by both heat and light, a 1,4-dihydropyridine derivative represented by the general formula:

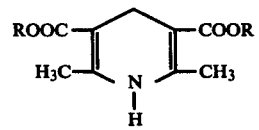

wherein R represents a straight or branched-chain saturated or unsaturated alkyl radical containing from 9 to 22 carbon atoms.

2. A composition according to claim 1, wherein the dihydropyridine derivative is present in an amount of from 0.01 to 0.2 percent by weight, based on the vinyl polymer or copolymer.

3. A composition according to claim 1, wherein the dihydropyridine derivative is present in an amount of from 0.01 to 0.2 percent by weight, based on the vinyl polymer or copolymer.

4. A composition according to claim 1, wherein the vinyl copolymer is a vinyl chloride-vinyl acetate copolymer.

5. A composition according to claim 1, wherein the vinyl copolymer is a vinyl chloride-vinylidene chloride copolymer.

6. An article produced from a synthetic resin composition according to claim 1.

7. An article as claimed in claim 6, the article being a food packaging material or container.

8. A method of stabilising a vinyl chloride homopolymer or copolymer which comprises incorporating in the vinyl polymer or copolymer from 0.01 to 0.5 percent by weight, based on the vinyl polymer or copolymer, of a 1,4-dihydropyridine derivative represented by the general formula:

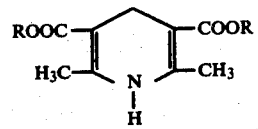

wherein R represents a straight or branched-chain saturated or unsaturated alkyl radical containing from 9 to 22 carbon atoms.

* * * * *